United States Patent [19]

Tarumi et al.

[11] Patent Number: 5,580,992

[45] Date of Patent: Dec. 3, 1996

[54] OLEFINIC MONOMERS CONTAINING PENDANT PERFLUORINATED CYCLIC ETHER MOIETIES

[75] Inventors: Yasuo Tarumi; Hirofumi Kishita; Toshio Takago, all of Matsuida-machi, Japan

[73] Assignee: Shin-Etsu Chemical Co., Ltd., Tokyo, Japan

[21] Appl. No.: 396,619

[22] Filed: Mar. 1, 1995

[30] Foreign Application Priority Data

Mar. 1, 1994 [JP] Japan .................................. 6-055279
Mar. 1, 1994 [JP] Japan .................................. 6-055280

[51] Int. Cl.⁶ ............................................... C07D 321/08
[52] U.S. Cl. ........................... 549/346; 549/347; 526/247
[58] Field of Search ......................... 526/247; 549/346, 549/347

[56] References Cited

U.S. PATENT DOCUMENTS

| | | | |
|---|---|---|---|
| 3,382,222 | 5/1968 | Pittman | 526/247 |
| 4,793,352 | 12/1988 | Eichenlaub | 128/399 |
| 5,254,699 | 10/1993 | Inomata | 549/380 |

*Primary Examiner*—C. Warren Ivy
*Assistant Examiner*—Garth M. Dahlen

*Attorney, Agent, or Firm*—Cushman Darby & Cushman, L.L.P.

[57] ABSTRACT

A fluorine-containing compound represented by the following general formula (1):

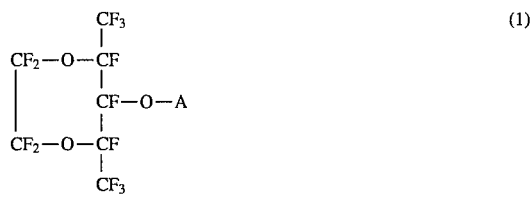

wherein A represents a group $-CH_2-CH=CH_2$ or a group

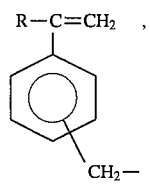

in which R represents a hydrogen atom or an alkyl group. The compound is useful as an intermediate for producing various compounds and can introduce perfluorocyclic ether groups into various polymers to give such properties as chemical resistance, water repellency, oil repellency, and weather resistance to the polymers.

6 Claims, 1 Drawing Sheet

OLEFINIC MONOMERS CONTAINING PENDANT PERFLUORINATED CYCLIC ETHER MOIETIES

BACKGROUND OF THE INVENTION

1. Field of the Invention

The present invention relates to novel fluorine-containing compounds, and more particularly to fluorine-containing compounds having a perfluorocyclic ether group and a method of producing the same.

2. Description of the Prior Art

Heretofore, as fluorine-containing styrene derivatives, compounds represented by the following general formula:

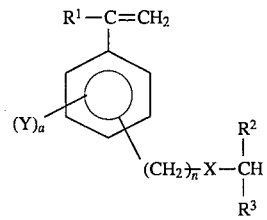

wherein $R^1$ represents a hydrogen atom or a lower alkyl group, $R^2$ represents a hydrogen atom or a fluorine-containing group, $R^3$ represents a fluorine-containing group, X represents —O— or >Si (R)$_2$ in which R represents a lower alkyl group, Y represents a halogen atom, n is 0 or 1, and a is an integer of 0 to 4 are known (see Japanese Pre-examination Patent Publication (KOKAI) Nos. 62-104814 and 62-289538).

The above fluorine-containing styrene derivatives can be homopolymerized or copolymerized with another polymerizable monomer to introduce a fluorine-containing group into various polymers and therefore very useful industrially.

However, specifically indicated fluorine-containing groups ($R^2$ and $R^3$) in the above fluorine-containing styrene derivatives are a polyfluoroalkyl group or a perfluoroalkyl group having 1 to 10 carbon atoms and a branched fluorooxyalkyl group having an ether linkage represented by the following formula:

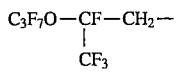

That is, styrene derivatives having a perfluorocyclic ether group are not known at all.

Hitherto, as organic compounds having a perfluorocyclic ether group, compounds represented by the following formula:

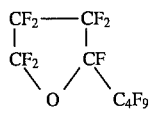

are known. Although these fluorine-containing organic compounds are used as an inactive liquid, the fluorine-containing compounds do not have a functional group and are poor in reactivity with other substances and therefore it cannot be expected to use the fluorine-containing compounds, for example, as a raw material for synthesis of other materials.

On the other hand, U.S. Pat. No. 4,033,984, U.S. Pat. No. 4,035,388, Japanese Patent Publication (KOKOKU) Nos. 59-42676, 60-15630, and 60-2291 disclose fluorine-containing compounds having a perfluorocyclic ether group and rich with reactivity derived from COF radical, represented by the following formula (i):

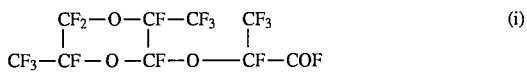

Further, perfluoro compounds represented by the following formulas (ii) and (iii):

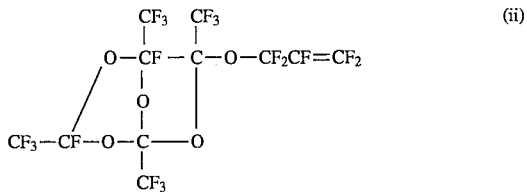

and

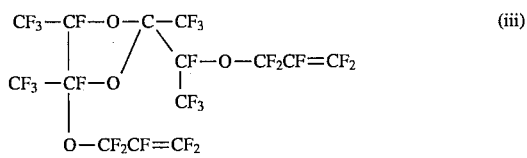

are reported (see GB Patent 1571356 A, Japanese Preexamination Patent Publication (KOKAI) No. 53-82713).

Since all of these compounds represented by the formulas (i) to (iii) have a perfluorocyclic ether group and a reactivity, they are expected to be used as a raw material for synthesis of other compounds. However, as compounds having a perfluorocyclic ether group, compounds having an allyl group (—CH$_2$CH=CH$_2$) or a group having an unsubstituted or lower alkyl-substituted stylyl group represented by the following general formula:

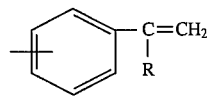

wherein R stands for a hydrogen atom or a lower alkyl group, are not known.

SUMMARY OF THE INVENTION

An object of the present invention is to provide novel and chemically quite stable fluorine-containing compounds having a perfluorocyclic ether group.

According to the present invention there is provided a fluorine-containing compound represented by the following general formula (1):

wherein A represents a group having the formula (2):

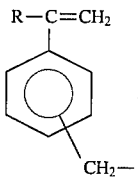
(2)

wherein R represents a hydrogen atom or an alkyl group, or a group —CH$_2$—CH=CH$_2$.

The present fluorine-containing compound having a perfluorocyclic ether group has a chemically stable structure and can be subjected to an addition reaction such as hydrosilylation, or homopolymerization or copolymerization with other olefinic monomers, using a free radical species, cation species or anion species as a polymerization initiator, to introduce the perfluorocyclic ether group into various compounds and polymers. In particular, if a fluorine-containing compound having an allyl group is used, by hydrosilylation reaction, for example, with a silicon compound having an SiH group or SiH groups such as, e.g., organohydrogensilanes and organohydrogenpolysiloxanes, an organosilicon compound into which a perfluorocyclic ether group is introduced can be synthesized. Since such a perfluorocyclic ether group exhibits such properties as chemical resistance, water repellency, oil repellency, and weather resistance, the present invention is very useful to improve such properties.

DETAILED DESCRIPTION OF THE PREFERRED EMBODIMENTS

Figure 1:
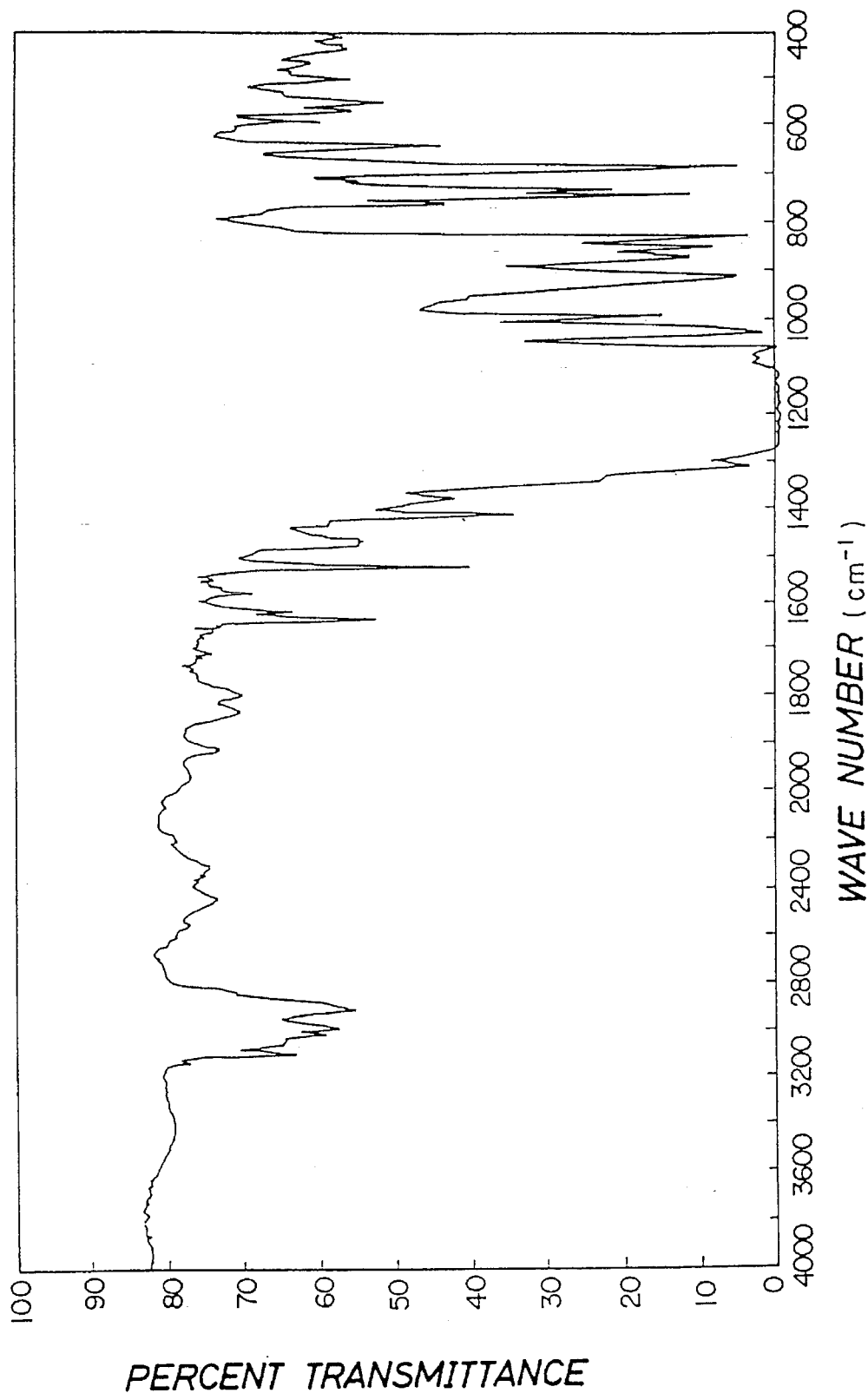
FIG. 1 is the IR chart of the present fluorine-containing compound obtained in Example 1.

The present fluorine-containing compound includes, as its embodiments, a fluorine-containing compound represented by the following general formula (3):

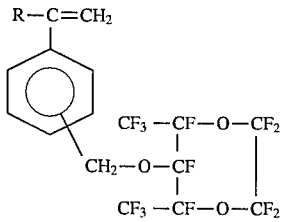
(3)

wherein R has the same meaning as defined for the formula (2), and a fluorine-containing compound represented by the formula (4):

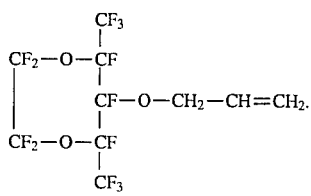
(4)

The alkyl group represented by R in the above general formulas (2) and (3) includes an alkyl group having 1 to 4 carbon atoms, such as methyl, ethyl, propyl, isopropyl, butyl, isobutyl, tert-butyl and the like. A preferable alkyl group is a lower alkyl group having 3 or less carbon atoms. Particularly preferred R in the formula (2) or (3) are a hydrogen atom and the methyl group in view of availability of raw materials or stability of products.

Since the compounds have a styrene structure or an allyl group in the molecule, they can be homopolymerized or copolymerized with other polymerizable monomer and are useful as a raw material for the production of a polymer having perfluorocyclic ether groups in the side chains or as pendant groups.

The fluorine-containing compound represented by the above general formula (1) can be produced, for example, by causing a perfluorocyclic ketone represented by the following formula (5):

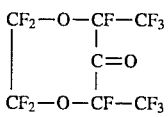
(5)

to react with a compound represented by the following formula (6):

A-Z (6)

wherein A has the same meaning as defined above and Z represents an eliminable group, in the presence of a fluoride anion source and a solvent.

The perfluorocyclic ketone represented by the above formula (5) is a known compound, is described, for example, in U.S. Pat. No. 5,247,101 and Japanese Pre-examination Patent Publication (KOKAI) No. 4-316576, and is synthesized in accordance with the method disclosed in the U.S. Patent or the Japanese Pre-examination Patent Publication.

The compound of the formula (6) includes, for example, a substituted or unsubstituted styrene compound having the general formula (7):

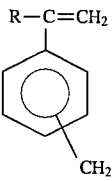
(7)

wherein R is as defined for the formula (2) and Z is as defined above, and an allyl compound of the formula:

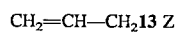
CH$_2$=CH—CH$_2$13 Z wherein Z is as defined above.

The eliminable group represented by Z in the above formula (6) includes, for example, a halogen atom such as a chlorine atom, a bromine atom and an iodine atom, and a tosyloxy group.

The allyl compound includes, for example, allyl chloride, allyl bromide, allyl iodide, and allyl p-toluenesulfonate.

Preferably, the compound represented by the above formula (6) is used generally in an amount of 0.3 to 1.5, preferably 1 to 1.5 moles per mole of the above perfluorocyclic ketone.

As the fluoride anion source, for example, an alkali fluoride, such as sodium fluoride, potassium fluoride, and cesium fluoride, and a quaternary ammonium salt, such as tetrabutylammonium fluoride, are preferably used. The fluoride anion source is preferably used in an amount of 1 to 1.5 moles per mole of the above perfluorocyclic ketone.

As the solvent, any solvent can be used so long as it is inactive for the reaction, and generally an aprotic polar solvent, such as glyme, diglyme, triglyme, tetraglyme, diethyl ether, tetrahydrofuran, dioxane, N,N-dimethylformamide, N,N-dimethylacetamide, and acetonitrile, is preferable. The amount of the solvent to be preferably used is 0.1 to 20 liters, preferably 0.5 to 20 liters per mole of the above perfluorocyclic ketone.

To carry out the reaction, out of the above raw material components, particularly the fluoride anion source and the solvent are previously dehydrated and then are used, which is desirable to allow the reaction to proceed smoothly. The reaction is carried out in such a way that these raw materials are mixed under nonaqueous conditions and are allowed to react at a temperature of 0 to 200° C., and preferably 30 to 150° C., for about 1 hour to 10 days with stirring. After the completion of the reaction, the obtained compound of the present invention can be isolated by means of distillation or the like.

The fluorine-containing compound represented by the above general formula (3) can be produced, for example, by causing a perfluorocyclic ketone represented by the above formula (5) to react with a styrene compound represented by the above formula (7) in the presence of the above fluoride anion source and the above solvent.

The compound represented by the above formula (4) can be produced, for example, by causing a perfluorocyclic ketone represented by the above formula (5) to react with the allyl compound in the presence of the above fluoride anion source and the above solvent.

Generally, the allyl compound is used preferably in an amount of 0.3 to 1.5 moles, more preferably 1.0 to 1.5 moles, per mole of the above perfluorocyclic ketone.

The solvent is used in an amount of preferably 0.1 to 20 liters, more preferably 0.5 to 20 liters, per mole of the above perfluorocyclic ketone.

EXAMPLES

Example 1

After 82.2 g (0.54 mole) of dehydrated cesium fluoride, 241 g of dehydrated tetraglyme, and 166.6 g (0.46 mole) of a perfluorocyclic ketone represented by the above formula (5) were charged into a 1-liter glass reactor, they were stirred under a nitrogen atmosphere at room temperature for 2 hours. Then 34.0 g (0.22 mole) of p-chloromethylstyrene and 20 mg of p-methoxyphenol (polymerization inhibitor) were added, and they were stirred under a nitrogen atmosphere at 95° C. for 11 hours.

The resulting reaction mixture was subjected to flash distillation under reduced pressure to obtain 210.9 g of a fraction. By GC analysis, it was confirmed that the fraction contained 6.1% of a desired product. The fraction was further distilled to isolate a product having a boiling point of 85° to 86° C. and the product was subjected to various analyses. As a result, it was confirmed that the product was a styrene derivative represented by the following formula (1a):

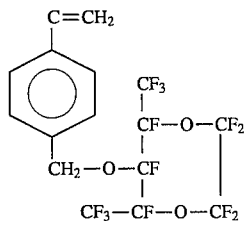

(1a)

The results of the analyses are shown below:
$^{19}$F-NMR: (CCl$_4$ solution, CF$_3$COOH standard)
 −57.5 to −51.9 ppm (m, 3F; >CF−)
 −9.0 to −2.3 ppm (m, 10F; —CF$_3$, —CF$_2$O—)
$^1$H-NMR: (CCl$_4$ solution, TMS standard)
 4.4 ppm (s, 2H; —CH$_2$O—)
 5.2 ppm (dd, 1H;

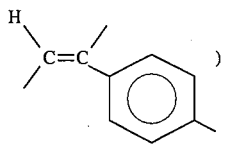

5.6 ppm (dd, 1H;

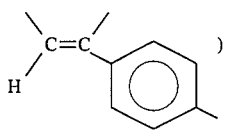

6.6 ppm (dd, 1H;

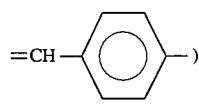

7.2 ppm (m, 4H;

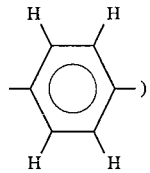

GC-MS:
 M$^+$=496, 117

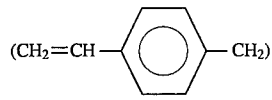

100 (C$_2$F$_4$), 69 (CF$_3$)
IR: shown in FIG. 1.

Example 2

18.0 g (50 mmol) of a perfluorocyclic ketone represented by the above formula (5), 9.9 g (65 mmol) of dehydrated cesium fluoride, 30 ml of dehydrated tetraglyme, and 6.0 g (50 mmol) of allyl bromide were charged into a 100-ml of glass reactor and they were stirred under a nitrogen atmosphere at 70° C. for 4 hours.

Then, the reaction mixture thus obtained was subjected to flash distillation with the reaction mixture heated to 50° C. under a reduced pressure of 2 mmHg and thus 10.5 g of a fraction was obtained. By GC analysis, it was confirmed that the fraction contained the desired product in an amount of 72%.

This fraction was distilled to isolate the product having a boiling point of 143° to 145° C. and various analyses of the fraction were carried out to confirm that the product was the compound represented by the above formula (4). The results of the analyses are shown below:
$^1$H-NMR: (CCl$_4$ solution, TMS standard)
 4.4 ppm (m, 2H; —CH$_2$—)
 5.1 to 5.4 ppm (m, 2H; CH$_2$=)
 5.6 to 6.2 ppm (m, 1H; =CH—)

$^{19}$F-NMR: (CCl$_4$ solution, CF$_3$COOH standard)

−57.4 to −52.8 ppm (m, 3F; >CF—)

−9.4 to −2.6 ppm (m, 10F; —CF$_2$O—, —CF$_3$)

IR:

1650 cm$^{-1}$ (CH$_2$=CH—)

GC-MS:

M$^+$=420, 69 (CF$_3$), 41 (C$_3$H$_5$)

What is claimed is:

1. A fluorine-containing compound represented by the following general formula (1):

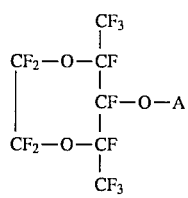

wherein A represents a group —CH$_2$—CH=CH$_2$ or a group

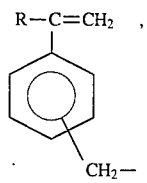

in which R represents a hydrogen atom or an alkyl group.

2. The fluorine-containing compound of claim 1, represented by the following general formula (3):

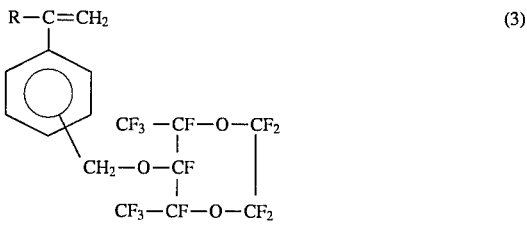

wherein R represents a hydrogen atom or an alkyl group.

3. The fluorine-containing compound of claim 1, represented by the following formula (4):

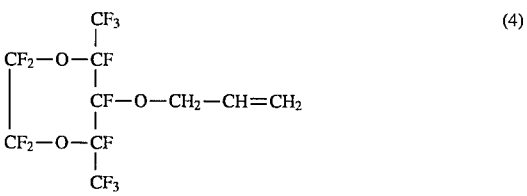

4. The fluorine-containing compound of claim 2, wherein R represents a hydrogen atom.

5. The fluorine-containing compound of claim 2, wherein R represents an alkyl group having 1 to 4 carbon atoms.

6. The fluorine-containing compound of claim 5, wherein said alkyl group is a lower alkyl group having 3 or less carbon atoms.

* * * * *